US007439064B2

(12) United States Patent
Thomson et al.

(10) Patent No.: US 7,439,064 B2
(45) Date of Patent: *Oct. 21, 2008

(54) CULTIVATION OF HUMAN EMBRYONIC STEM CELLS IN THE ABSENCE OF FEEDER CELLS OR WITHOUT CONDITIONED MEDIUM

(75) Inventors: James A. Thomson, Madison, WI (US); Mark Levenstein, Madison, WI (US)

(73) Assignee: Wicell Research Institute, Inc., Madison, WI (US)

( * ) Notice: Subject to any disclaimer, the term of this patent is extended or adjusted under 35 U.S.C. 154(b) by 308 days.

This patent is subject to a terminal disclaimer.

(21) Appl. No.: 11/078,737

(22) Filed: Mar. 11, 2005

(65) Prior Publication Data

US 2005/0244962 A1 Nov. 3, 2005

Related U.S. Application Data

(63) Continuation-in-part of application No. 10/952,096, filed on Sep. 28, 2004, now abandoned, which is a continuation-in-part of application No. 09/522,030, filed on Mar. 9, 2000, now Pat. No. 7,005,252.

(51) Int. Cl.
*C12N 5/02* (2006.01)
*C12N 5/08* (2006.01)
(52) U.S. Cl. ............... 435/377; 435/366; 435/384; 435/387; 435/389
(58) Field of Classification Search ............... 435/366, 435/377, 383
See application file for complete search history.

(56) References Cited

U.S. PATENT DOCUMENTS

| 5,405,772 | A | 4/1995 | Ponting |
| 5,453,357 | A | 9/1995 | Hogan |
| 5,670,372 | A | 9/1997 | Hogan |
| 5,690,926 | A | 11/1997 | Hogan |
| 5,750,376 | A | 5/1998 | Weiss et al. |
| 5,817,773 | A | 10/1998 | Wilson et al. |
| 5,843,780 | A | 12/1998 | Thomson |
| 6,200,806 | B1 | 3/2001 | Thomson |
| 6,245,566 | B1 | 6/2001 | Gearhart et al. |
| 7,005,252 | B1 * | 2/2006 | Thomson ............... 435/1.1 |
| 7,297,539 | B2 * | 11/2007 | Mandalam et al. ........... 435/394 |
| 2002/0081724 | A1 | 6/2002 | Carpenter et al. |
| 2002/0137204 | A1 | 9/2002 | Carpenter et al. |
| 2003/0017589 | A1 | 1/2003 | Mandalam et al. |
| 2003/0073234 | A1 | 4/2003 | Amit et al. |
| 2003/0190748 | A1 | 10/2003 | Thomson |
| 2004/0235159 | A1 | 11/2004 | Mandalam et al. |
| 2008/0020458 | A9 * | 1/2008 | Mandalam et al. ........... 435/366 |

FOREIGN PATENT DOCUMENTS

| DE | 197 56 864 C1 | 12/1997 |
| WO | WO 97/47734 | 12/1997 |
| WO | WO 98/30679 | 7/1998 |
| WO | WO 99/20740 | 4/1999 |
| WO | WO 99/20741 | 4/1999 |
| WO | WO 00/68359 | 11/2000 |
| WO | WO 01/66697 A2 | 9/2001 |
| WO | WO 03/020920 A1 | 3/2003 |
| WO | WO 2004/099394 | 11/2004 |

OTHER PUBLICATIONS

Amit, M., et al., "Feeder Layer- and Serum-Free Culture of Human Embryonic Stem Cells," Biology of Reproduction 70:837-845 (2004).
Li, Y., et al., "Expansion of Human Embryonic Stem Cells in Defined Serum-Free Medium....," Biotechnology and Bioengineering, Wiley & Sons 91:688-698 (2005).
Beattie, G.M., et al., "Activin A maintains Pluripotency of Human Embryonic Stem Cells in the Absence of Feeder Layers," Stem Cells 23:489-495 (2005).
Boilly, B., et al., "FGF signals for cell proliferation and migration through different pathways," Cytokine & Growth Factor Reviews 11:295-302 (2000).
Clark, A.J., et al., "Germ line manipulation: applications in agriculture and biotechnology," Transgenic Animals (1992).
Gleveland, W.L., et al., "Routine large-Scale production of Monoclonal Antibodies in a Protein-Free Culture Medium," J. of Immunological Methods 56:221-234 (1983).
Cruz, Y.P., et al., "Origin of Embryonic and Extraembryonic Cell Lineages in Mammalian Embryos," Embryonic and Extraembryonic Cell Lineages 147-204 (1991).

(Continued)

*Primary Examiner*—Deborah Crouch
(74) *Attorney, Agent, or Firm*—Quarles & Brady LLP

(57) ABSTRACT

The invention relates to methods for culturing human embryonic stem cells by culturing the stem cells in an environment essentially free of mammalian fetal serum and in a stem cell culture medium including amino acids, vitamins, salts, minerals, transferring, insulin, albumin, and a fibroblast growth factor that is supplied from a source other than just a feeder layer the medium. Also disclosed are compositions capable of supporting the culture and proliferation of human embryonic stem cells without the need for feeder cells or for exposure of the medium to feeder cells.

10 Claims, No Drawings

OTHER PUBLICATIONS

Froud, S.J., "The Development, Benefits and Disadvantages of Serum-Free Media," Dev. Biol. Stand. Basel, Karger 99:157-166 (1999).

Gearhart, J., "Cell Biology: New Potential for Human Embryonic Stem Cells," Science 282:1061-1052 (1998).

Goldsborough, M.D., et al., "Serum-Free Culture of Murine Embryonic Stem (ES) Cells," Focus 20:8-12 1998).

Klimanskaya, I., et al., "Human embryonic stem cells derived without feeder cells," The lancet 365:1636-1641 (2005).

Mummery, C.L., et al., "Fibroblast growth factor-mediated growth regulation and receptor expression in . . . ," Biochem-Biophys-Res-Commun. 191-188-95 (1993).

Nichols, J., et al., "Establishment of germ-line-competent embryonic stem (ES) cells using differentiation inhibiting activity," Development 110:1341-1348 (1990).

Ornitz, D.M., et al., "Receptor Specificity of the Fibroblast Growth Factor Family," J. of Biological Chemistry 271:15292-15297 (1996).

Pease, S., et al., "Isolation of Embryonic Stem (ES) Cells in media Supplemented with Recombinant Leukemia Inhibitory Factor (LIF)," Developmental Biology 141:344-32 (1990).

Piedrahita, J.A., et al., "On the Isolation of Embryonic Stem Cells: Comparative Behavior of Murine, Porcine and Ovine Embryos," Theriogenology 34:879-901 (1990).

Rossant, J., et al., "In search of the tabula rasa of human cells," Nature Biotechnology 17:23-24 (1999).

Thomson, J.A., et al., "Isolation of a primate embryonic stem cell line," Proc. Natl. Acad. Sci. USA 92:7844-7848 (1995).

Thomson, J.A., et al., "Embryonic Stem Cell Lines Derived from Human Blastocysts," Science Magazine 282:1145 (1997).

Xie, M-H., et al., "FGF-19, A Novel Fibroblast Growth Factor with Unique Specificity for FGFR4," Cytokine 11:729-735 (1999).

Xu, C., et al., "Feeder-free growth of undifferentiated human embryonic stem cells," Technical Report 971-974 (2001).

Yamaguchi, T.P., et al., "Expression of the Fibroblast Growth Factor Receptor FGFR-1/flg during Gastrulation and Segmentation in the Mouse Embryo," Developmental biology 152:75-88 (1992).

* cited by examiner

CULTIVATION OF HUMAN EMBRYONIC STEM CELLS IN THE ABSENCE OF FEEDER CELLS OR WITHOUT CONDITIONED MEDIUM

CROSS REFERENCES TO RELATED APPLICATIONS

This application is a continuation-in-part of application of U.S. patent application Ser. No. 10/952,096, filed Sep. 28, 2004 now abandoned which is a continuation-in-part application of U.S. patent application Ser. No. 09/522,030 filed Mar. 9, 2000 now U.S. Pat. No. 7,005,252.

STATEMENT REGARDING FEDERALLY SPONSORED RESEARCH

To be determined.

BACKGROUND OF THE INVENTION

The present invention relates to methods for culturing primate embryonic stem cell cultures and culture media useful therewith.

Primate (e.g. monkey and human) pluripotent embryonic stem cells have been derived from preimplantation embryos. See, for example, U.S. Pat. No. 5,843,780 and J. Thomson et al., 282 Science 1145-1147 (1998). The disclosure of these publications and of all other publications referred to herein are incorporated by reference as if fully set forth herein. Notwithstanding prolonged culture, these cells stably maintain a developmental potential to form advanced derivatives of all three embryonic germ layers.

Primate (particularly human) ES cell lines have widespread utility in connection with human developmental biology, drug discovery, drug testing, and transplantation medicine. For example, current knowledge of the post-implantation human embryo is largely based on a limited number of static histological sections. Because of ethical considerations the underlying mechanisms that control the developmental decisions of the early human embryo remain essentially unexplored.

Although the mouse is the mainstay of experimental mammalian developmental biology, and although many of the fundamental mechanisms that control development are conserved between mice and humans, there are significant differences between early mouse and human development. Primate/human ES cells should therefore provide important new insights into their differentiation and function.

Differentiated derivatives of primate ES cells could be used to identify gene targets for new drugs, used to test toxicity or teratogenicity of new compounds, and used for transplantation to replace cell populations in disease. Potential conditions that might be treated by the transplantation of ES cell-derived cells include Parkinson's disease, cardiac infarcts, juvenile-onset diabetes mellitus, and leukemia. See e.g. J. Rossant et al. 17 Nature Biotechnology 23-4 (1999) and J. Gearhart, 282 Science 1061-2 (1998).

Long term proliferative capacity, developmental potential after prolonged culture, and karyotypic stability are key features with respect to the utility of primate embryonic stem cell cultures. Cultures of such cells (especially on fibroblast feeder layers) have typically been supplemented with animal serum (especially fetal bovine serum) to permit the desired proliferation during such culturing.

For example, in U.S. Pat. Nos. 5,453,357, 5,670,372 and 5,690,296 various culture conditions were described, including some using a type of basic fibroblast growth factor together with animal serum. Unfortunately, serum tends to have variable properties from batch to batch, thus affecting culture characteristics.

In WO 98/30679 there was a discussion of providing a serum-free supplement in replacement for animal serum to support the growth of certain embryonic stem cells in culture. The serum replacement included albumins or albumin substitutes, one or more amino acids, one or more vitamins, one or more transferrins or transferrin substitutes, one or more antioxidants, one or more insulins or insulin substitutes, one or more collagen precursors, and one or more trace elements. It was noted that this replacement could be further supplemented with leukemia inhibitory factor, steel factor, or ciliary neurotrophic factor. Unfortunately, in the context of primate embryonic stem cell cultures (especially those grown on fibroblast feeder layers), these culture media did not prove satisfactory.

In the context of nutrient serum culture media (e.g. fetal bovine serum), WO 99/20741 discusses the benefit of use of various growth factors such as bFGF in culturing primate stem cells. However, culture media without nutrient serum are not described.

In U.S. Pat. No. 5,405,772 growth media for hematopoietic cells and bone marrow stromal cells are described. There is a suggestion to use fibroblast growth factor in a serum-deprived media for this purpose. However, conditions for growth of primate embryonic stem cells are not described.

The first human embryonic stem cell cultures were grown using a layer of fibroblast feeder cells, which has the property of enabling the human embryonic stem cells to be proliferated while remaining undifferentiated. Later, it was discovered that it is sufficient to expose the culture medium to feeder cells, to create what is called conditioned medium, which had the same property as using feeder cells directly. Without the use of either feeder cells or conditioned medium, human embryonic stem cells in culture could not be maintained in an undifferentiated state. Since the use of feeder cells, or even the exposure of the medium to feeder cells, risks contamination of the culture with unwanted material, avoiding the use of feeder cells and conditioned medium is desirable. Medium which has not been exposed to feeder cells is referred to here as unconditioned medium.

It can therefore be seen that a need still exists for techniques to stably culture primate embryonic stem cells without the requirement for use of animal serum.

BRIEF SUMMARY OF THE INVENTION

In one aspect the invention provides a method of culturing primate embryonic stem cells. One cultures the stem cells in a culture essentially free of mammalian fetal serum (preferably also essentially free of any animal serum) and in the presence of fibroblast growth factor that is supplied from a source other than just a fibroblast feeder layer. In a preferred form, the fibroblast feeder layer, previously required to sustain a stem cell culture, is rendered unnecessary by the addition of sufficient fibroblast growth factor.

Fibroblast growth factors are essential molecules for mammalian development. There are currently more then twenty known fibroblast growth factor ligands and five signaling fibroblast growth factor receptors therefor (and their spliced variants). See generally D. Ornitz et al., 25 J. Biol. Chem. 15292-7 (1996); U.S. Pat. No. 5,453,357. Slight variations in these factors are expected to exist between species, and thus the term fibroblast growth factor is not species limited. However, we prefer to use human fibroblast growth factors, more preferably human basic fibroblast growth factor produced from a recombinant gene. This compound is readily available in quantity from Gibco BRL-Life Technologies and others.

It should be noted that for purposes of this patent the culture may still be essentially free of the specified serum even though a discrete component (e.g. bovine serum albumin) has been isolated from serum and then is exogenously supplied. The point is that when serum itself is added the variability concerns arise. However, when one or more well defined purified component(s) of such serum is added, they do not.

Preferably the primate embryonic stem cells that are cultured using this method are human embryonic stem cells that are true ES cell lines in that they: (i) are capable of indefinite proliferation in vitro in an undifferentiated state; (ii) are capable of differentiation to derivatives of all three embryonic germ layers (endoderm, mesoderm, and ectoderm) even after prolonged culture; and (iii) maintain a normal karyotype (are euploid) throughout prolonged culture. These cells are therefore referred to as being pluripotent.

The culturing permits the embryonic stem cells to stably proliferate in culture for over one month (preferably over six months; even more preferably over twelve months) while maintaining the potential of the stem cells to differentiate into derivatives of endoderm, mesoderm, and ectoderm tissues, and while maintaining the karyotype of the stem cells.

In another aspect the invention provides another method of culturing primate embryonic stem cells. One cultures the stem cells in a culture essentially free of mammalian fetal serum (preferably also essentially free of any animal serum) and in the presence of a growth factor capable of activating a fibroblast growth factor signaling receptor, wherein the growth factor is supplied from a source other than just a fibroblast feeder layer. While the growth factor is preferably a fibroblast growth factor, it might also be other materials such as certain synthetic small peptides (e.g. produced by recombinant DNA variants or mutants) designed to activate fibroblast growth factor receptors. See generally T. Yamaguchi et al., 152 Dev. Biol. 75-88 (1992)(signaling receptors).

In yet another aspect the invention provides a culture system for culturing primate embryonic stem cells. It has a human basic fibroblast growth factor supplied by other than just the fibroblast feeder layer. The culture system is essentially free of animal serum.

Yet another aspect of the invention provides cell lines (preferably cloned cell lines) derived using the above method. "Derived" is used in its broadest sense to cover directly or indirectly derived lines.

Variability in results due to differences in batches of animal serum is thereby avoided. Further, it has been discovered that avoiding use of animal serum while using fibroblast growth factor can increase the efficiency of cloning.

It is therefore an advantage of the present invention to provide culture conditions for primate embryonic stem cell lines where the conditions are less variable and permit more efficient cloning. Other advantages of the present invention will become apparent after study of the specification and claims.

DETAILED DESCRIPTION OF THE PREFERRED EMBODIMENTS

In some of the following experiments one of the inventors here used the methods and culture systems of the invention to culture human ES cell lines without adding serum to the culture medium. Two clonally derived human ES cell lines proliferated for over eight months after clonal derivation and maintained the ability to differentiate to advanced derivatives of all three embryonic germ layers when cultured in a medium without serum as a constituent.

In another of the experiments set forth below, it has now been demonstrated that the addition of relatively large amounts of a human fibroblast growth factor (FGF) aids in the culture and growth of human embryonic stem cells, even in the absence of both serum and feeder cells. This permits the culture of stem cells that have never been exposed either to animal cells or to media in which animal cells have been cultured. These stem cell cultivation conditions (i.e. no feeder cells and no conditioned medium) are referred to here as feeder independent. Prior culture conditions have been described, based on the use of medium conditioned with feeder cells, which are described as feeder free. However, the use of conditioned medium does not resolved the dependence on the use of feeder cells, which still must be used to condition the medium. The techniques described here permit the indefinite and feeder independent culture of human embryonic stem cells having normal karyotype and with the stem cells remaining undifferentiated.

Techniques for the initial derivation, culture, and characterization of the human ES cell line H9 were described in J. Thomson et al., 282 Science 1145-1147 (1998). The experiments described below were conducted with this and other cell lines, but the processes and results are independent of the particular ES cells lines.

It is described here that the addition of fibroblast growth factor (FGF) aids in the cultivation and cloning of human ES cells. The addition of FGF is important in two distinct regards. First, the addition of FGF at moderate levels (e.g. 4 ng/ml) permits the culture of undifferentiated human ES cells in a medium devoid of serum. At this level, the rate of differentiation of the stem cell is slowed, compared to lower levels of FGF, but the cells will eventually differentiate. Secondly, the addition of FGF at higher levels makes the culture conditions of the medium feeder independent, in that no feeder cells are required at all to indefinitely maintain the pluripotency of euploid undifferentiated human ES cells in culture.

This first phenomenon is believed to be actuated by the action of FGF in interacting with FGF receptors in the human ES cells. To avoid the use of serum, it is not particularly critical which of the many known FGF variants are used in the culture. Here basic FGF, or bFGF, also known as FGF2, is commonly used, but that is only because bFGF is one of the readily commercially available members of the FGF family of factors. More than twenty different FGF family members have been identified, and they are referred to as FGF-1 through FGF-27. While the concentration of FGF here is given in amounts of bFGF, it should be understood that this is intended to quantify the amount of stimulation of the FGF receptors and that the concentration of FGF may have to be adjusted, upward or downward, for other members of the FGF family. For bFGF, the preferred concentration of FGF in the ES cell medium is in the range of about 0.1 to about 1000 ng/ml, with concentrations in excess range of about 4 ng/ml being useful to avoid the need for serum in the medium.

Surprisingly, it has been found that for the second attribute of FGF in a human ES cell medium, the selection of the variant of FGF has some criticality. For this purpose it has been found that when the concentration of bFGF is about 100 ng/ml, this condition is sufficient to avoid the need for both serum and feeder cells, making the culture feeder independent. For this purpose, it has been found that FGF family members FGF2 (bFGF), FGF4, FGF9, FGF17 and FGF18 are each sufficient at 100 ng.ml of culture to make the human ES cell culture feeder independent. By contrast, it has been found that FGF family members FGF1 (acidic FGF), FGF1β, FGF3, FGF5, FGF6, FGF7, FGF8, FGF10, FGF16, FGF19, and FGF20 are not sufficient at 100 ng/ml to support feeder independence. We believe, but do not have present data, that the results using these forms of FGF is not a result of concentration and that higher concentrations of the particular FGF also would not succeed in supporting feeder independence. For FGF9, our data suggests that at this level (100 ng/ml) FGF9 supports human ES cell culture but the data has been slightly more equivocal.

The exact minimal amount of the effective variants of FGF that will suffice to support human ES cells as feeder independent in culture is not known with precision at this time, but can be determined by empirical testing. It is known that for FGF2, that 4 ng/ml added to the medium alone is insufficient for the indefinite maintenance of euploid undifferentiated human ES cells in culture, while 100 ng/ml of FGF2 alone in the medium is sufficient. While ES cells grown in unconditioned medium containing as little as 4 ng/ml will remain undifferentiated for some time, and perhaps a passage or two, the cells will eventually begin to differentiate. In our hands, the ability of a medium to culture ES cells to remain indefinitely undifferentiated and euploid is demonstrated when the cells are cultured for at least six passages while remaining proliferating, undifferentiated, euploid and while maintaining the characteristic morphology of human ES cells. As used here, a maintenance concentration of an FGF is the concentration of that FGF necessary to support the maintenance of human ES cells in an undifferentiated, euploid and proliferating state for at least six passages. For FGF2, the minimal maintenance concentration is between 4 ng/ml and 100 ng/ml and the exact minimal maintenance concentration can be determined by using the protocols below to interpolate those amounts. For each other effective FGF, e.g. FGF4, FGF9, FGF17, and FGF18, the corresponding minimal maintenance concentration for each FGF can be determined by similar testing.

Human ES cell cultures in the defined human ES cell media described below in the examples can be cultivated indefinitely in the complete absence of fibroblast feeder cells and without conditioned media while remaining euploid. The ES cells are thus truly feeder independent. The human ES cells retain all of the characteristics of human ES cells including characteristic morphology (small and compact with indistinct cell membranes), proliferation and the ability to differentiate into many, if not all, the cell types in the human body. The human ES cells will also retain the characteristic that they can form all three primordial cell layers when injected into immunocompromised mice. In particular, the ES cells retain the ability to differentiate into ectoderm, mesoderm and endoderm. The ES cells still exhibit markers indicative of ES cell status, such as expression of the nuclear transcription factor Oct4, which is associated with pluripotency. Throughout the process and at its end, the human ES cells retain normal karyotypes.

EXAMPLES

In the first experiments described here human ES cells were plated on irradiated (35 gray gamma irradiation) mouse embryonic fibroblasts. Culture medium for the present work consisted of 80% KNOCKOUT™ Dulbeco's modified Eagle's medium (DMEM) (Gibco BRL, Rockville, Md.), 1 mM L-Glutamine, 0.1 mM β-mercaptoethanol, and 1% non-essential amino acids stock (Gibco BRL, Rockville, Md.), supplemented with either 20% fetal bovine serum (HyClone, Logan, Utah) or 20% KNOCKOUT™ serum replacement (SR), a serum-free replacement originally optimized for mouse ES cells (Gibco BRL, Rockville, Md.). The components KNOCKOUT™ SR are those described for serum replacements in WO 98/30679.

In alternative experiments medium was supplemented with either serum or the aforesaid serum replacer KNOCKOUT™ SR, and either with or without human recombinant basic fibroblast growth factor (bFGF, 4 ng/ml). The preferred concentration range of bFGF in the culture was between 0.1 ng/ml to 500 ng/ml.

To determine cloning efficiency under varying culture conditions, H-9 cultures were dissociated to single cells for 7 minutes with 0.05% trypsin/0.25% EDTA, washed by centrifugation, and plated on mitotically inactivated mouse embryonic fibroblasts ($10^5$ ES cells per well of a 6-well plate). To confirm growth from single cells for the derivation of clonal ES cell lines, individual cells were selected by direct observation under a stereomicroscope and transferred by micropipette to individual wells of a 96 well plate containing mouse embryonic fibroblasts feeders with medium containing 20% serum replacer and 4 ng/ml bFGF.

Clones were expanded by routine passage every 5-7 days with 1 mg/ml collagenase type IV (Gibco BRL, Rockville, Md.). Six months after derivation, H9 cells exhibited a normal XX karyotype by standard G-banding techniques (20 chromosomal spreads analyzed). However, seven months after derivation, in a single karyotype preparation, 16/20 chromosomal spreads exhibited a normal XX karyotype, but 4/20 spreads demonstrated random abnormalities, including one with a translocation to chromosome 13 short arm, one with an inverted chromosome 20, one with a translocation to the number 4 short arm, and one with multiple fragmentation. Subsequently, at 8, 10, and 12.75 months after derivation, H9 cells exhibited normal karyotypes in all 20 chromosomal spreads examined.

We observed that the cloning efficiency of human ES cells in previously described culture conditions that included animal serum was poor (regardless of the presence or absence of bFGF). We also observed that in the absence of animal serum the cloning efficiency increased, and increased even more with bFGF. It has now been established that the addition of FGF facilitated the cultivation of human ES cells in general and is of particular help in facilitating the cloning of human ES cultures.

The data expressed below is the total number of colonies resulting from $10^5$ individualized ES cells plated, +/− standard error of the mean (percent colony cloning efficiency). With 20% fetal serum and no bFGF there was a result of 240+/−28. With 20% serum and bFGF (at 4 ng/ml) the result was about the same, 260+/−12. In the absence of the serum (presence of 20% serum replacer) the result with no bFGF was 633+/−43 and the result with bFGF was 826+/−61. Thus, serum adversely affected cloning efficiency, and the presence of the bFGF in the absence of serum had an added synergistic benefit insofar as cloning efficiency.

The long term culture of human ES cells in the presence of serum does not require the addition of exogenously supplied bFGF, and (as noted above) the addition of bFGF to serum-containing medium does not significantly increase human ES cell cloning efficiency. However, in serum-free medium, bFGF increased the initial cloning efficiency of human ES cells.

Further, it has been discovered that supplying exogenous bFGF is very important for continued undifferentiated proliferation of primate embryonic stem cells in the absence of animal serum. In serum-free medium lacking exogenous bFGF, human ES cells uniformly differentiated by two weeks of culture. Addition of other factors such as LIF (in the absence of bFGF) did not prevent the differentiation.

The results perceived are particularly applicable to clonal lines. In this regard, clones for expansion were selected by placing cells individually into wells of a 96 well plate under direct microscopic observation. Of 192H-9 cells plated into wells of 96 well plates, two clones were successfully expanded (H-9.1 and H-9.2). Both of these clones were subsequently cultured continuously in media supplemented with serum replacer and bFGF.

H9.1 and H9.2 cells both maintained a normal XX karyotype even after more than 8 months of continuous culture after cloning. The H-9.1 and H-9.2 clones maintained the potential to form derivatives of all three embryonic germ layers even after long term culture in serum-free medium. After 6 months of culture, H9.1 and H9.2 clones were confirmed to have normal karyotypes and were then injected into SCID-beige mice.

Both H9.1 and H9.2 cells formed teratomas that contained derivatives of all three embryonic germ layers including gut epithelium (endoderm) embryonic kidney, striated muscle, smooth muscle, bone, cartilage (mesoderm), and neural tissue (ectoderm). The range of differentiation observed within the teratomas of the high passage H9.1 and H9.2 cells was comparable to that observed in teratomas formed by low passage parental H9 cells.

It should be appreciated from the description above that while animal serum is supportive of growth it is a complex mixture that can contain compounds both beneficial and detrimental to human ES cell culture. Moreover, different serum batches vary widely in their ability to support vigorous undifferentiated proliferation of human ES cells. Replacing serum with a clearly defined component reduces the variability of results associated with this serum batch variation, and should allow more carefully defined differentiation studies.

Further, the lower cloning efficiency in medium containing serum suggests the presence of compounds in conventionally used serum that are detrimental to stem cell survival, particularly when the cells are dispersed to single cells. Avoiding the use of these compounds is therefore highly desired.

Feeder Independent Culture

Additional investigations later were directed to the culture of ES cell lines in higher concentrations of FGF but in the absence of both serum and feeder cells. Three different medium formulations have been used in this work, and those medium formulations are referred to here as UM100, BM+ and DHEM. The nomenclature UM100 refers to unconditioned medium to which has been added 100 ng/ml of bFGF. The UM100 medium does contain the Gibco KNOCKOUT™ SR product but does not include or require the use of fibroblast feeder cells of any kind. The BM+ medium is basal medium (DMEM/F12) plus additives, described below, that also permits the culture of cells without feeder cells, but this medium omits the serum replacer product. Lastly, the name DHEM refers to a defined human embryonic stem cell medium. This medium, also described below, is sufficient for the culture, cloning and indefinite proliferation of human ES cells while being composed entirely of inorganic constituents and only human proteins, as opposed to the BM+ medium which contains bovine albumin.

Culture of Human ES Cells Lines H1 and H9 in UM100/BM+/DHEM

UM100 media was prepared as follows: unconditioned media (UM) consisted of 80% (v/v) DMEM/F12 (Gibco/Invitrogen) and 20% (v/v) KNOCKOUT™ SR (Gibco/Invitrogen) supplemented with 1 mM glutamine (Gibco/Invitrogen), 0.1 mM β-mercaptoethanol (Sigma—St. Louis, Mo.), and 1% nonessential amino acid stock (Gibco/Invitrogen). To complete the media 100 ng/ml bFGF was added and the medium was filtered through a 0.22 μM nylon filter (Nalgene).

BM+ medium was prepared as follows: 16.5 mg/ml BSA (Sigma), 196 μg/ml Insulin (Sigma), 108 μg/ml Transferrin (Sigma), 100 ng/ml bFGF, 1 mM glutamine (Gibco/Invitrogen), 0.1 mM β-mercaptoethanol (Sigma), and 1% nonessential amino acid stock (Gibco/Invitrogen) were combined in DMEM/F12 (Gibco/Invitrogen) and the osmolality was adjusted to 340 mOsm with 5M NaCl. The medium was then filtered through a 0.22 uM nylon filter (Nalgene).

DHEM medium was prepared as follows: 16.5 mg/ml HSA (Sigma), 196 μg/ml Insulin (Sigma), 108 μg/ml Transferrin (Sigma), 100 ng/ml bFGF, 1 mM glutamine (Gibco/Invitrogen), 0.1 mM β-mercaptoethanol (Sigma), 1% nonessential amino acid stock (Gibco/Invitrogen), vitamin supplements (Sigma), trace minerals (Cell-gro®), and 0.014 mg/L to 0.07 mg/L selenium (Sigma), were combined in DMEM/F12 (Gibco/Invitrogen) and the osmolarity was adjusted to 340 mOsm with 5M NaCl. It is noted that the vitamin supplements in the medium may include thiamine (6.6 g/L), reduced glutathione (2 mg/L) and ascorbic acid $PO_4$. Also, the trace minerals used in the medium are a combination of Trace Elements B (Cell-gro®, Cat #: MT 99-175-Cl and C (Cell-gro®, Cat #: MT 99-176-Cl); each of which is sold as a 1,000× solution. It is well known in the art that Trace Elements B and C contain the same composition as Cleveland's Trace Element I and II, respectively. (See Cleveland, W. L., Wood, I. Erlanger, B. F., *J. Imm. Methods* 56: 221-234, 1983.) The medium was then filtered through a 0.22 uM nylon filter (Nalgene). Finally, sterile, defined lipids (Gibco/Invitrogen) were added to complete the medium.

H1 or H9 human embryonic stem cells previously growing on MEF (mouse embryonic fibroblast) feeder cells were mechanically passaged with dispase (1 mg/ml) and plated onto Matrigel (Becton Dickinson, Bedford, Mass.). Appropriate medium was changed daily until cell density was determined to be adequate for cell passage. Cells were then passaged with dispase as described and maintained on Matrigel (Becton Dickinson).

Growth Rates

To determine the growth rate of human ES cells in the various media, cells were plated at a density of about $5 \times 10^5$ cells/well in triplicate in 6-well tissue culture dishes (Nalgene). On days 3, 5, and 7 the triplicate wells were treated with trypsin/EDTA (Gibco/Invitrogen), individualized and cell numbers were counted. On day 7, additional wells were treated with trypsin, counted, and used to re-seed a new plate at a cell density of about $2 \times 10^5$ cells/well. The day 7 cultures, which had been trypsin processed, were analyzed for ES cell surface markers Oct4, SSEA4, and Tra1-60 by FACS analysis. Growth rates were collected for 3 consecutive passages. Growth rate experiments show that UM100-cultured human ES cells grow as robustly as CM-cultured human ES cells.

Attachment Dynamics

To determine the attachment rate of human ES cells in the various media cells were plated at a density of $2 \times 10^5$ cells/well in a 6-well tissue culture dish (Nalgene). At time points ranging from 30 minutes to 48 hours unattached cells were washed away and attached cells were removed with trypsin/EDTA (Gibco/Invitrogen) and counted. These experiments were performed to examine if the UM100 growth rate data was due to a combination of better cell attachment and slower growth as opposed to equivalent growth rates for UM100 and CM. We found that attachment percentages were equivalent for both media at all time points tested. Thus, they grow at the same rate.

FACS Analysis of Human ES Cells

Human ES cells were removed from a 6-well tissue culture plate (Nalgene) with trypsin/EDTA (Gibco/Invitrogen)+2% chick serum (ICN Biomedicals, Inc., Aurora, Ohio) for 10 min. at 37° C. The cells were diluted in an equal volume of FACS Buffer (PBS+2% FBS+0.1% Sodium Azide) and filtered through an 80 μM cell strainer (Nalgene). Pellets were collected for 5 min. at 1000 RPM and resuspended in 1 ml 0.5% paraformaldehyde. Human ES cells were fixed for 10 min. at 37° C. and the pellets were collected as described. The ES cells were resuspended in 2 ml FACS Buffer and total cell number was counted with a hemacytometer. Cells were pelleted as described and permeablized for 30 min. on ice in 90% methanol. Human ES cells were pelleted as described and $1 \times 10^5$ cells were diluted into 1 ml of FACS Buffer+0.1% Triton X-100 (Sigma) in a FACS tube (Becton Dickinson). hESC were pelleted as described and resuspended in 50 μl of primary antibody diluted in FACS Buffer+0.1% Triton X-100 (Sigma). Samples of appropriate control antibodies were applied in parallel. hESC were incubated overnight at 4° C. Supernatants were poured off and cells were incubated in the dark for 30 min. at room temperature in 50 μl of secondary antibody (Molecular Probes/Invitrogen). FACS analysis was performed in a Facscalibur (Becton Dickinson) cell sorter with CellQuest Software (Becton Dickinson). This method for performing FACS analysis allows one to detect cell surface markers, to thus show that you have ES cells. The result observed was that human ES cells cultured in UM100 were 90% positive for Oct-4 as a population. This is comparable to CM-cultured ES cells and confirms that the cells are an ES cell population. For the analysis of SSEA4 and Tra1-60, the process was performed as for Oct-4, except that the cells were not treated in paraformaldehyde or methanol. After cell staining, the cells were re-suspended in FACS buffer (without Triton) and analyzed as described with appropriate antibodies in FACS buffer, again without Triton. The undifferentiated ES cell cultures averaged about 90% positive for these two cell surface markers as well. This was demonstrated by FACS analysis discussed above.

Results

Cells of human ES cell line H1 have now been cultivated in the UM100 medium for over 33 passages (over 164 population doublings) while retaining the morphology and characteristics of human ES cells. H1 cells were cultivated in the BM+ medium for over 6 passages (70 days) while retaining the morphology and characteristics of human ES cells. H9 cells have been cultivated in DHEM medium for over 5 passages (67 days). H9 and H7 human ES cells were also cultivated in UM100 medium in an undifferentiated state for 22 passages and 21 passages respectively. Subsequent testing of the BM+ and UM100-cultured cells established normal karyotypes.

Study of Forms of FGF

Human ES cells of line H1 were cultured under standard conditions in conditioned medium for three passages before being switched to the test media. For the test conditions, cells were cultured on conditioned medium for 24 hours (day 0) and then switched to the test media the next day (day 1). Thereafter the cells were cultured in the respective test media. The human ES cell line H9 was also cultured on Matrigel in conditioned media for five passages before being switched to the test media in parallel.

The cells were passaged using the following procedures. The cell cultures were grown to suitable densities (which took approximately 7 days) in 6 well tissue culture plates and then the cultures were treated with 1 ml Dipase (1 mg/ml) (Gibco/Invitrogen) for 5-7 minutes at 37° C. The Dipase was then removed and replaced with 2 ml of the appropriate growth medium. Using a 5 ml pipette, the cells were mechanically removed from the tissue culture plate and then dispersed by pipetting. The cells were then pelleted in a clinical centrifuge for 5 minutes at 1000 rpm. The pellet was then re-suspended in an appropriate volume of medium and replated at desired dilution.

The media formulation was consistent other than the selection of FGF added. The base medium was UM100, with the FGF being variable depending on the desired test condition. The following FGF variants were tested, each added to the medium at 100 ng/ml: FGF1 (acidic FGF), FGF1β (isoform of acidic FGF), FGF2 (basic FGF), FGF3, FGF4, FGF5, FGF6, FGF7, FGF8, FGF9, FGF10, FGF16, FGF17, FGF18, FGF19, FGF20. All FGFs were purchased commercially or produced in recombinant hosts.

The competence of the particular FGF form to support human ES cell cultures was judged after each passage. The conditions which were judged to support human ES cell culture supported cultures that proliferated appropriately in an undifferentiated state in culture, independent of feeder cells, could be passaged effectively, and continued to express the human ES cell markers Oct4, SSEA4, and Tra1-60. The conditions which were judged not to support human ES cells in culture gave rise to cultures in which significant differentiation of the cells was apparent by morphological observation, and the cells were unable to proliferate upon colony passage. The FGF variants which supported human ES cell culture were FGF2, FGF4, FGF17 and FGF18. The FGF variants which did not support maintenance of the human ES cells in an undifferentiated state were FGF1, FGF1B, FGF3, FGF5, FGF6, FGF7, FGF8, FGF10, FGF16, FGF19 and FGF20. The results for the medium with FGF9 added were initially on the margin. Upon repeating the procedure, it appears likely that FGF9 supplemented at 100 ng/ml can also support undifferentiated human ES cells in culture.

At the present time, media supplemented with FGF4, FGF17 and FGF20 have supported undifferentiated human ES cell cultures of H1 cells for 8 passages. Similar replicates with FGF4, FGF9, FGF17, and FGF18 on human ES cell lines H9 and H14 have extended for 3 and 2 passages respectively.

The present invention has been described above with respect to its preferred embodiments. Other forms of this concept are also intended to be within the scope of the claims. For example, while recombinantly produced human basic fibroblast growth factor was used in the above experiments, naturally isolated fibroblast growth factor should also be suitable. Further, these techniques should also prove suitable for use on monkey and other primate cell cultures.

Thus, the claims should be looked to in order to judge the full scope of the invention.

INDUSTRIAL APPLICABILITY

The present invention provides methods for culturing primate embryonic stem cells, and culture media for use therewith.

We claim:

1. A method of culturing human embryonic stem cells, comprising:
   culturing human embryonic stem cells on a matrix in a culture medium free of serum and in a stem cell culture medium containing amino acids, vitamins, salts, minerals, transferrin or a transferrin substitute, insulin or an insulin substitute, albumin, and a fibroblast growth factor supplied from a source other than a feeder layer, the fibroblast growth factor present in a concentration at least as high as a maintenance concentration, wherein the medium supports the culture and proliferation of undifferentiated proliferating euploid human embryonic stem cells for at least six passages without feeder cells or conditioned medium.

2. The method of claim 1 wherein the FGF is selected from FGF2, FGF4, FGF9, FGF17 and FGF18.

3. The method of claim 1 wherein the FGF is FGF2 which is present in the medium at 100 ng/ml.

4. A method of culturing human embryonic stem cells in defined media without serum and without feeder cells on a matrix, the method comprising:

culturing human embryonic stem cells in a culture medium containing albumin, amino acids, vitamins, minerals, at least one transferrin or transferrin substitute, at least one insulin or insulin substitute, the culture medium free of serum and containing at least about 100 ng/ml of a fibroblast growth factor, and culturing without feeder cells or conditioned medium, wherein the medium supports proliferation of the human embryonic stem cells in an undifferentiated state.

5. The method of claim 4, wherein said culturing step includes the embryonic stem cells proliferating in culture for over one month while maintaining the potential of the embryonic stem cells to differentiate into derivatives of endoderm, mesoderm, and ectoderm tissues, and while maintaining the karyotype of the embryonic stem cells.

6. The method of claim 4 wherein the FGF is selected from FGF2, FGF4, FGF9, FGF17 and FGF18.

7. A culture of human embryonic stem cells comprising:
human embryonic stem cells, a matrix; and
a stem cell medium containing albumin, amino acids, vitamins, minerals, at least one transferrin or transferrin substitute, at least one insulin or insulin substitute, the culture medium free of serum and containing a fibroblast growth factor supplied from a source other than a feeder layer, the fibroblast growth factor present in a concentration at least as high as a maintenance concentration, wherein the medium supports the culture of the embryonic stem cells indefinitely in the absence of serum and in the absence of feeder cells and also in the absence of medium exposed to feeder cells,
wherein the culture maintains the embryonic stem cells in an undifferentiated state indefinitely with normal karyotype.

8. The culture of claim 7 wherein the fibroblast growth factor is FGF2 which is present in the medium in a concentration of at least about 100 ng/ml.

9. A culture of feeder independent human embryonic stem cells comprising
human embryonic stem cells on a matrix in a stem cell culture medium, the stem cell culture medium comprising albumin, amino acids, vitamins, minerals, at least one transferrin or transferrin substitute, at least one insulin or insulin substitute, the culture medium free of serum and containing a fibroblast growth factor present in a concentration at least as high as a maintenance concentration, wherein the fibroblast growth factor is selected from FGF2, FGF4, FGF9, FGF17, and FGF18, wherein the culture is independent of feeder cells while the human embryonic stem cells remain euploid and in an undifferentiated state.

10. A culture as claimed in claim 9 wherein the fibroblast growth factor is present at a concentration of at least about 100 ng/ml.

* * * * *